United States Patent
Buzug et al.

(10) Patent No.: US 6,445,771 B1
(45) Date of Patent: Sep. 3, 2002

(54) X-RAY DEVICE INCORPORATING DETECTION OF SHUTTER EDGES

(75) Inventors: Thorsten Buzug, Kiel; Michael Kuhn, Hamburg; Rafael Wiemker, Kisdorf, all of (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/561,474

(22) Filed: Apr. 27, 2000

(30) Foreign Application Priority Data

Apr. 30, 1999 (DE) .......................... 199 19 849

(51) Int. Cl.⁷ ................................. G21K 1/04
(52) U.S. Cl. ................ 378/150; 378/160; 378/163; 378/164; 378/207; 378/205
(58) Field of Search ................. 378/150, 160, 378/163, 164, 207, 205

(56) References Cited

U.S. PATENT DOCUMENTS 3,639,764 A * 2/1972 Olson et al. .............. 378/193
4,817,125 A * 3/1989 Sklebitz ..................... 378/152
5,960,102 A * 9/1999 Van Eeuwijk et al. ...... 382/128

FOREIGN PATENT DOCUMENTS

| DE | 19539602 A | 4/1997 | .......... G03B/42/02 |
| DE | 19637918 A | 4/1998 | .......... A61B/6/00 |

* cited by examiner

Primary Examiner—David P. Porta
Assistant Examiner—Pamela R. Hobden
(74) Attorney, Agent, or Firm—John Vodopia

(57) ABSTRACT

The shutters (2) in an X-ray device which include at least a radiation source (1), a diaphragm device (8) with shutters (2) and a recording (3) and image processing unit (4), are provided with hole and/or edge patterns (11–14) which reproduce non-anatomical patterns in the radiation image; the shutter edges (15) are detected in the radiation image in the image processing unit on the basis of such patterns, so that only the directly irradiated part of the patient is displayed.

8 Claims, 1 Drawing Sheet

X-RAY DEVICE INCORPORATING
DETECTION OF SHUTTER EDGES

BACKGROUND OF THE INVENTION

1. Field of the Invention

The invention relates to an X-ray device which includes at least one radiation source, a diaphragm device with shutters, and a recording and image processing unit.

2. Description of Related Art

The X-ray dose whereto a patient is exposed during an examination by means of X-rays should be kept as small as possible. To this end, the beam is restricted by a diaphragm device. The evaluation of an X-ray image necessitates a faithful reproduction of even the smallest differences in the gray tones.

DE 195 39 602 A1 describes an X-ray examination apparatus provided with two adjustable diaphragm devices. A first diaphragm device restricts an X-ray beam which is generated by an X-ray source, traverses an examination zone and subsequently passes through a second diaphragm device before it is incident on a unit for recording the X-ray image. The second diaphragm device is constructed so that it can be seen in the X-ray image whether the X-ray beam defined by the first diaphragm device is significantly larger than the X-ray beam defined by the second diaphragm device. To this end, the shutters of the second diaphragm device are provided with indentations which extend perpendicularly to the edges of the shutters and form strip-like projections at the edge of the X-ray image. It is thus achieved that the X-ray image has a well-defined boundary, because the definition by means of the first diaphragm device only leads to unsharp edges of the X-ray image. The second diaphragm device, being arranged at a small distance from and in front of the unit for recording the X-ray image, ensures that the edges of the shutters are sharply imaged in the X-ray image.

DE 196 37 918 A1 describes an X-ray device for medical applications in which means for generating a device-specific and/or component-specific mark or data symbol are automatically assigned to an image to be formed. They concern recesses, marks or punctures which are reproduced in the image in such a manner that the images can be identified on the basis thereof during later observation by the physician; such marks can also provide the physician with additional information concerning the image.

The definition of the beam path by means of the diaphragm device produces edges in the radiation image which separate the area traversed by X-rays from the area not traversed thereby. The complete radiation image exhibits many different black-white transitions or gray tone transitions which are formed on the one hand by gray tone transitions at, for example bones, but on the other hand also by the edges of the shutters. For the evaluation of the radiation image, however, the physician requires only the exposed area. The evaluation of the overall radiation image may lead to false interpretations, because different gray tones caused by scattering are also reproduced in the non-exposed area.

Citation of a reference herein, or throughout this specification, is not to construed as an admission that such reference is prior art to the Applicant's invention of the invention subsequently claimed.

SUMMARY OF THE INVENTION

It is an object of the invention to detect the edges of the shutters in order to reproduce only the exposed area for the observation of the radiation image.

This object is achieved in that the shutters are provided with hole and/or edge patterns which reproduce non-anatomical patterns in the radiation image and that the image processing unit is arranged to detect the shutter edges in the radiation image.

The shutters are provided with hole and/or edge patterns which do not occur in human anatomy. The shutters are arranged in the beam path of the radiation source in such a manner that the part of the patient irradiated by the rays is limited from the outside. To this end, the shutters are arranged so as to be movable in the diaphragm device. The displacement of the shutters can take place manually or also automatically by means of adjusting motors which are driven by a control circuit. The hole patterns are provided in the shutters at a known distance from the edge. The hole patterns, consisting of a plurality of holes, are transparent to radiation and hence are reproduced in the radiation image. The edge patterns are provided at the edges of the shutters and also have a non-anatomical shape which is also reproduced in the radiation image. After having passed the shutters, the radiation traverses the part of the patient to be examined. The radiation is then influenced or absorbed by the tissue and the bones of the patient, and is subsequently incident on the recording unit in which a radiation image is formed which contains on the one hand the hole and/or edge patterns and on the other hand different gray tones, since the radiation is absorbed to a different extent because of the different density of tissues and bones.

The radiation image is applied to the image processing unit. Therein the radiation image is examined for the known hole and/or edge patterns which will be referred to hereinafter merely as patterns. Because the patterns do not have an anatomical shape, mix-ups with, for example, transitions from bones to soft tissue can be precluded during the edge detection. After the known patterns have been found, the position of the edges in the radiation image is calculated on the basis of the known arrangement of the patterns in the shutters. The edges of the shutters reproduce a comparatively strong gray tone transition in the radiation image, so that it can be unambiguously identified by way of such a calculation. After the detection of the edges of the shutters, the areas of the radiation image which are situated outside these edges are suppressed and not displayed to the observer. A display unit shows the observer only the part of the patient which has been traversed by the radiation, so that for the diagnosis the observer will not include gray tone transitions caused by scattering of the radiation. The radiation dose whereto the patient is exposed is thus reduced to a necessary minimum.

In a preferred embodiment of the invention the hole pattern is realized in the form of perforations. The hole patterns are then arranged in several rows which extend parallel to the edge of the shutter. The hole patterns have a different arrangement in each row. The distances between the individual holes as well as the diameter and the shape of the holes can be varied. By using different types of perforations, the pattern thus reproduced in the radiation image can be adapted to the relevant application, so that in the case of imaging of given objects a perforation can be selected whose reproduction in the radiation image is unambiguously distinct from the imaged object and hence mix-ups are precluded during the edge detection.

In a preferred embodiment of the invention information is encoded in the perforations. When a plurality of parallel rows of perforations are reproduced in the radiation image, the magnitude of the covered area in the radiation image is encoded for example, by way of an increasing spacing of the holes in the rows of perforations. The detection of the edges in the image processing unit then yields further information as to how much surface area of the maximum possible radiation image area is covered by the shutters.

BRIEF DESCRIPTION OF THE DRAWINGS

Embodiments of the invention will be described in detail hereinafter with reference to the drawings. Therein.

DETAILED DESCRIPTION OF THE PREFERRED EMBODIMENT

Figure 1:
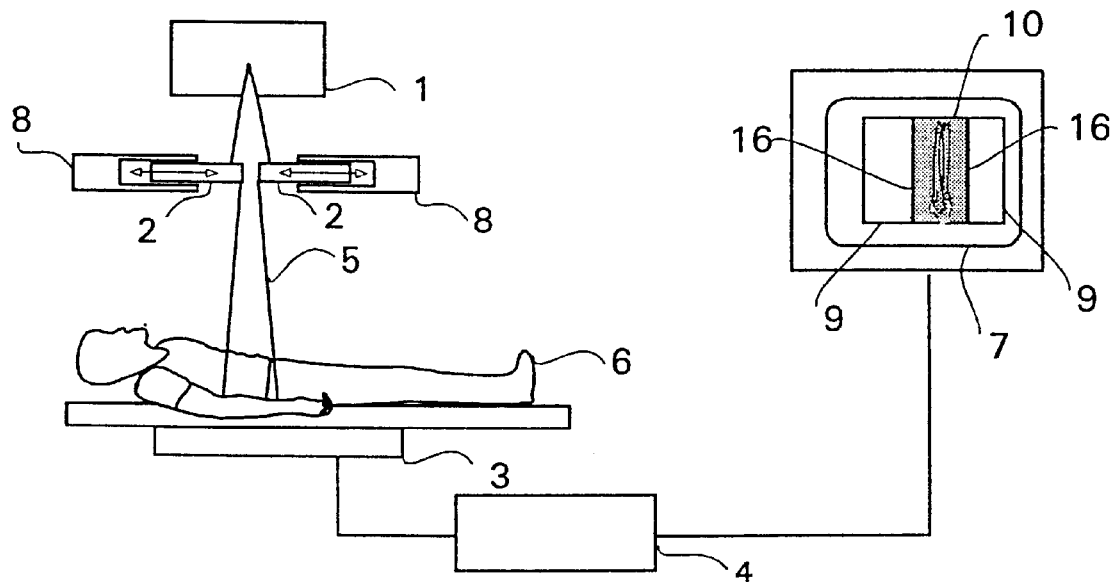
FIG. 1 is a diagrammatic representation of the X-ray device according to the invention.

FIG. 1 shows the X-ray device which includes a radiation source 1 for generating X-rays. The radiation emitted by the radiation source is incident on the shutters 2 which are journaled so as to be slidable in a diaphragm device 8. The shutters 2 are provided with non-anatomical, unambiguously recognizable perforations and/or edge patterns which cannot be shown in FIG. 1.

The shutters 2 define the beam path 5 so that the beam is incident on the part of the patient 6 which is to be examined by means of X-rays. The X-rays traverse the patient 6 and are absorbed to a different extent by tissue and bones of different density. The X-rays of different intensity thus produced are incident on the detector unit 3. In the detector unit the radiation image is recorded and applied to the image processing unit 4. The radiation image is searched for hole and/or edge patterns in the image processing unit 4, said patterns being provided in the shutters 2 and being transparent to X-rays so that they are reproduced in the radiation image. After such patterns have been found, the position 16 of the edges 15 of the shutters 2 is identified on the basis of the known arrangement of the hole and/or edge patterns in the shutters 2. The edges 15 are reproduced with a large difference in gray value tone in the radiation image; such a difference can also occur at the transition from bones to soft tissue. The position 16 of the edges 15 can be unambiguously determined by means of the hole and/or edge patterns. Only the irradiated part 10 of the patient with, for example the bones to be examined is then reproduced on a display unit 7. The area 9 covered by the shutters 2 is not displayed.

Figure 2:
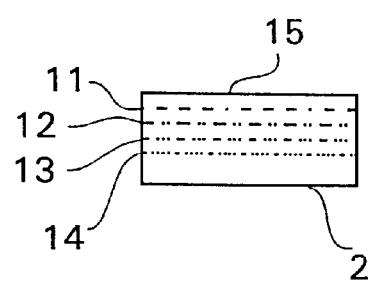
FIGS. 2 and 3 show different shutters.
Figure 3:
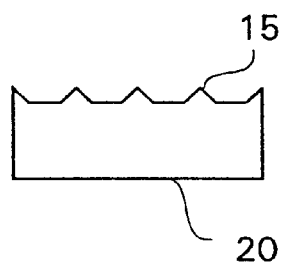

The FIGS. 2 and 3 show two shutters 2 and 20 which are used to limit the beam path 5.

The shutter 2 is provided with perforations which are transparent to X-rays. In each of the rows of perforations 11 to 14 there is a different, characteristic spacing of the holes. Information concerning the magnitude of the area to be covered is encoded in such different spacing of the holes. In the row of perforations 11 only one circular hole is provided in a series of elongate holes. This row of perforations 11 is situated at a single distance from the edge 15. The row of perforations 12 includes two holes and an elongate hole and is situated at twice the distance from the shutter edge 15. The row of perforations 13 includes three holes and is situated at three times the distance and the row of perforations 14 has a succession of four holes and is situated at four times the distance from the shutter edge 15.

The shutter 20 in FIG. 3 has an edge 15 which can be particularly simply recognized in the radiation image. The shutter 20 is provided with indentations which are situated at a regular distance from one another. Such indentations are detected at least as an interruption in a long, straight edge segment by means of a standard edge detection algorithm. This ensures that they are reliably distinguished from anatomical edges in the radiation image. An additional verification of the recognized shutter edges can be performed on the basis of the known imaging geometry of the X-ray device by calculating in advance the spacing and/or position of the indentations in the radiation image, followed by comparison with the result detected in the radiation image. The edge 15 can be described by a mathematical function.

Figure 4:
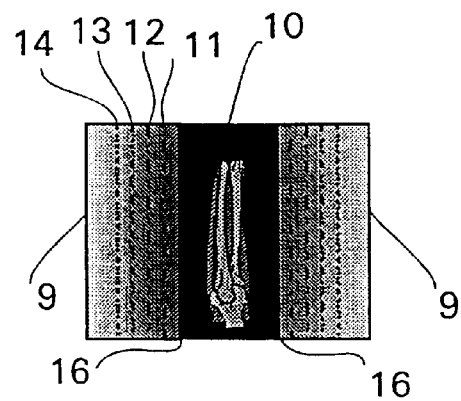
FIG. 4 shows a radiation image with non-anatomical patterns.

FIG. 4 shows a radiation image in which the edge areas 9 are covered by shutters 2. Because the rows of perforations 11 to 14 are now visible, only a minimum area was irradiated by the X-rays. The shutters 2 in the diaphragm device 8 were moved very far into the beam path 5. The rows of perforations 11 to 14 are situated at known distances from the relevant edge 15 of the shutters 2 detected in the radiation image.

In the image processing unit 4 the radiation image is searched for the reproductions of the patterns formed in the shutters 2, said search being performed on the basis of a pattern recognition algorithm. The radiation image is recorded typically by means of a digital detector. The values representative of the individual pixels are applied to the image processing unit 4. The radiation image, presented in digital form, is searched for a series of gray tones correlated with the rows of perforations 11 to 14 of the shutters 2. When such series of gray tones have been identified, the position 16 of the edge 15 of the shutter 2 in the radiation image is detected on the basis of the known distance between the relevant row of perforations 11 to 14 and the edge 15 of the shutter 2. The areas 9 of the radiation image which are covered by the shutters 2 are not shown on the display unit 7.

Consequently, during the evaluation of the X-ray image of the patient 6 the physician will not be distracted by gray tones outside the irradiated area which are due to scattering.

For radiography of artificial joints or prostheses the hole or edge patterns should be selected so that the artificial shapes are clearly distinct from the hole or edge patterns.

All references cited herein, as well as the priority document German Patent Application 19919849.7 filed Apr. 30, 1999, are incorporated herein by reference in their entirety and for all purposes to the same extent as if each individual publication or patent or patent application was specifically and individually indicated to be incorporated by reference in its entirety for all purposes.

What is claimed is:

1. An X-ray device comprising:

at least one radiation source, a diaphragm device with shutters, the shutters comprising hole and/or edge patterns which reproduce non-anatomical patterns in a radiation image, a recording unit and an image processing unit which is arranged to detect the hole and/or edge patterns of the shutters in the radiation image.

2. An X-ray device as claimed in claim 1, wherein the hole patterns comprise perforations which are arranged in rows extending parallel to the edge of the shutter, the spacing of the holes being different in each row of perforations.

3. An X-ray device as claimed in the claim 1 wherein the rows of perforations encode information.

4. An X-ray device as claimed in claim 3 wherein the information comprises the dimensions of the area covered by the shutters in the radiation image.

5. A diaphragm device for use in an X-ray device comprising shutters, wherein the shutters further comprise non-anatomical hole and/or edge patterns.

6. The device of claim 2 wherein the rows of perforations encode information.

7. The device of claim 6 wherein the information comprises the dimensions of the area covered by the shutters in the radiation image.

8. The device of claim 1 wherein the edge patterns comprise regularly spaced indentations.

* * * * *